(12) United States Patent
Bauss (10) Patent No.: US 12,296,157 B2
(45) Date of Patent: May 13, 2025

(54) INFORMATION CARRIER READER ASSEMBLY

(71) Applicant: SHL MEDICAL AG, Zug (CH)

(72) Inventor: Markus Bauss, Lengdorf (DE)

(73) Assignee: SHL Medical AG, Zug (CH)

( * ) Notice: Subject to any disclaimer, the term of this patent is extended or adjusted under 35 U.S.C. 154(b) by 1130 days.

(21) Appl. No.: 15/734,289

(22) PCT Filed: Sep. 12, 2019

(86) PCT No.: PCT/EP2019/074304
§ 371 (c)(1),
(2) Date: Dec. 2, 2020

(87) PCT Pub. No.: WO2020/064339
PCT Pub. Date: Apr. 2, 2020

(65) Prior Publication Data
US 2021/0220573 A1    Jul. 22, 2021

(30) Foreign Application Priority Data

Sep. 24, 2018 (EP) .................................. 18196316

(51) Int. Cl.
*H04B 5/26* (2024.01)
*A61M 5/50* (2006.01)

(52) U.S. Cl.
CPC ............ *A61M 5/5086* (2013.01); *H04B 5/26* (2024.01); *A61M 2205/3592* (2013.01); *A61M 2205/60* (2013.01)

(58) Field of Classification Search
CPC ........ A61M 5/2053; A61M 5/20; A61M 5/32; A61M 2205/502; A61M 2205/60; A61M 2205/3592; A61M 2205/3569; H04B 5/26
See application file for complete search history.

(56) References Cited

U.S. PATENT DOCUMENTS

| 9,311,592 | B1 * | 4/2016 | Vitello ............. G06K 19/07798 |
| 2008/0033368 | A1 * | 2/2008 | Fago ...................... G16H 20/13 |
| | | | 604/189 |

(Continued)

FOREIGN PATENT DOCUMENTS

| EP | 2962715 A1 | 1/2016 | |
| EP | 3184135 A1 * | 6/2017 | .......... A61M 5/2033 |

(Continued)

OTHER PUBLICATIONS

International Search Report and Written Opinion for Int. App. No. PCT/EP2019/074304, mailed Oct. 15, 2019.

*Primary Examiner* — Patrick C Chen
(74) *Attorney, Agent, or Firm* — McDonnell Boehnen & Berghoff LLP (57) ABSTRACT

An information carrier reader assembly is presented having a first antenna, a second antenna electrically connected to the first antenna, the first antenna attached to a first area of a medicament delivery device, where the medicament delivery device has an information carrier having a fourth antenna wherein the first antenna is positioned so as to enable transmission between the fourth and the first antenna. The information carrier reader assembly further has an information reader provided with an third antenna and being operably arranged to a second area of the medicament delivery device, wherein the second antenna is attached to the second area of the medicament delivery device, enabling a transmission between the second antenna and the third antenna.

9 Claims, 7 Drawing Sheets

(56) References Cited

U.S. PATENT DOCUMENTS

2015/0318623 A1* 11/2015 Laight ................... H01Q 1/02
                                                                      343/853
2017/0319787 A1* 11/2017 Roedle ................ A61M 5/3129

FOREIGN PATENT DOCUMENTS

| WO | 2016/055305 A1 | 4/2016 |
| WO | 2018/010931 A1 | 1/2018 |

* cited by examiner

INFORMATION CARRIER READER ASSEMBLY

CROSS REFERENCE TO RELATED APPLICATIONS

The present application is a U.S. National Phase Application pursuant to 35 U.S.C. § 371 of International Application No. PCT/EP2019/074304 filed Sep. 12, 2019, which claims priority to European Patent Application No. 18196316.6 filed Sep. 24, 2018. The entire disclosure contents of these applications are herewith incorporated by reference into the present application.

TECHNICAL AREA

The technical area pertains to medicament delivery devices provided with smart functions capable of collecting information from the medicament delivery devices and from elements contained therein.

BACKGROUND

In line with the current trends of developing smart primary containers and the like for medicament delivery devices, so-called rigid needle shields or RNS are used with syringes in particular for self-administration. In this regard, the RNS may be arranged with an RFID tag. Such solutions are described in the document WO 2018/010931, in which the RFID tag preferably is fixedly attached to and RNS through co-molding for instance. It is however conceivable that the RFID tag is attached to the RNS via adhesive labels and the like. The RFID tag may also be glued to a surface of the RNS. The important aspect is that the RFID is difficult to remove from the RNS. With this solution it is possible to obtain data that has been written to the RFID tag throughout the entire life cycle of the device, including assembly, packaging, storing, distribution and use.

The RFID tag may be read by external RFID readers at many different locations and situations throughout the life cycle as mentioned. However, there is also a strong trend to develop medicament delivery devices provided with "smart" functions. These functions may comprise detecting activation of the device, injection sequence and end of injection and may connect these to time stamps, thereby obtaining data regarding for instance adherence to a treatment scheme. The smart functions may then also comprise alerts to a user when a dose is to be administered according to the scheme. All this data obtained can then be transmitted to external sources for data handling. In some cases the smart functions may also comprise RFID readers in the medicament delivery device that can obtain drug specific data from e.g. medicament containers and/or RNS's attached to these medicament containers. This data can then be used for instance to alert a user that a medicament in the medicament container is about to expire for instance or what type of drug that is contained in the medicament container.

When looking at medicament delivery devices that are disposed after use, it is more difficult to include smart functions without the device becoming overly expensive. One solution is then to provide a unit that is releasably attachable to a medicament delivery device. One such solution is disclosed in the document WO 2017/032586. Here a recording unit is provided that is attachable to one end of a medicament delivery device, preferably the distal end. One reason for this is to have the recording interfering as little as possible when the medicament delivery device is used.

Another reason is the activation of the recording unit that may be performed when components of the medicament delivery device are moved during use. Since most components of the medicament delivery device move in the longitudinal direction during use, this may be utilized to let components move distally and thereby affect and activate the recording unit.

This solution has proven very useful and cost-efficient because the recording unit can be used with a large number of disposable medicament delivery devices. However, it has shown some drawbacks and shortcomings for some functions. For instance, the recording unit may be arranged with an RFID-reader for reading RFID-tags on for instance primary packages. However, if the medicament delivery device is assembled with a medicament container having an RNS with an RFID-tag, the reading distance from the distal end of the medicament delivery device with the recording unit attached is too long for the RNS-reader. Thus, valuable data from the RFID on the RNS cannot be obtained by the recording unit.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

The aim of the present application is to remedy the drawbacks of the state of the art solutions. This aim is solved by an application comprising the features of the independent claims. Preferable embodiments form the subject of the dependent patent claims.

According to one aspect, an RFID-reader assembly is provided comprising a first antenna and a second antenna electrically connected to the first antenna. The first antenna may be attached to a first area of a medicament delivery device, which medicament delivery device comprises an information carrier comprising a fourth antenna. The first antenna may be positioned so as to enable transmission between the fourth and the first antenna.

The information carrier reader assembly may further comprise an information reader provided with a third antenna and being operably arranged to a second area of the medicament delivery device. The second antenna may be attached to the second area of the medicament delivery device, enabling a transmission between the second antenna and the third antenna.

With this solution, an extension is obtained between the information carrier and the information carrier reader, where otherwise the distance between them would be too long.

According to one aspect, the first antenna may be a metal coil capable of providing an inductive coupling with the fourth antenna of the information carrier and that the second antenna is a metal coil capable of providing an inductive coupling with the third antenna of the information carrier reader. The metal coils solution is rather inexpensive and yet practical and may be used in disposable medicament delivery devices without making the production cost overly high.

In order to obtain the extension, the first antenna and the second antenna may be interconnected by conductive conduits. In this respect, the first antenna, the second antenna and the conductive conduits may be arranged on at least one adhesive label attachable to the medicament delivery device. Further in this regard, the at least one adhesive label may comprise a ruptable area forming a tamper indicating element.

The use of adhesive labels is a cheap yet very functional solution that does not affect the manufacturing of the medicament delivery device as such. The adhesive label may be attached as a final assembly or production step.

As an alternative, the conductive conduits may be formed on the medicament delivery device by laser direct structuring.

Further, the information carrier reader may be arranged on a re-usable part of the medicament delivery device and that the first antenna and the second antenna may be arranged on a disposable part of the medicament delivery device, wherein the third antenna of the information carrier reader may be capable of reading the second antenna when the disposable part is connected to the re-usable part.

As an alternative, the first antenna and second antenna may be arranged on the medicament delivery device and wherein the information carrier reader may be arranged in a separate unit releasably attachable to the medicament delivery device, wherein the third antenna of the information carrier reader is capable of reading the second antenna when the separate unit is connected to the medicament delivery device.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

In the description below and in the claims of the present application, the wording first part and second part of the medicament delivery device will be used. It is to be understood that the definition of the first part and the second part comprises both physically different components of the medicament delivery device but also different parts of one physical entity. Thus one single housing component may comprise two parts with this definition, for instance a proximal area of the housing forming the first part and a distal area of the housing forming the second part.

Figure 1:
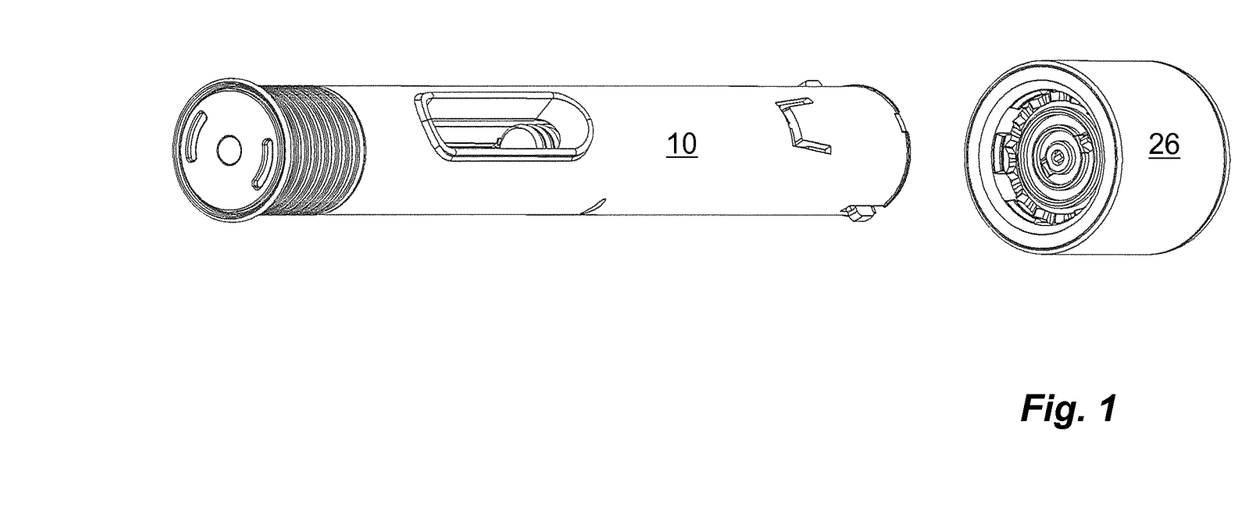
FIG. 1 shows a medicament delivery device provided with an attachable recording unit which may comprise the present application.
Figure 2:
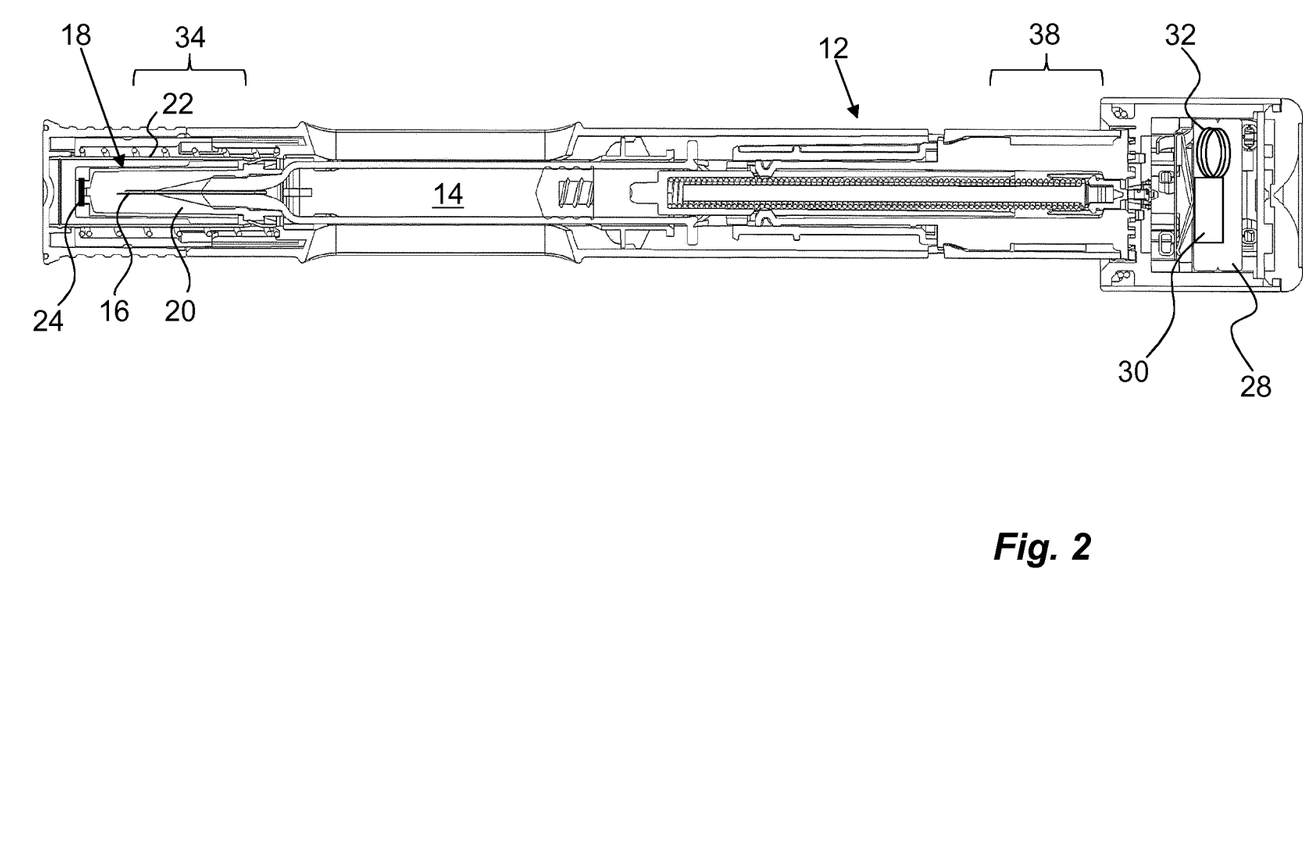
FIG. 2 shows a cross-section of the medicament delivery device according to FIG. 1 with the recording unit attached.

One embodiment where the present application is useful is for devices that are connected somehow. FIGS. 1 and 2 show a medicament delivery device 10 provided with some type of drive mechanism or power pack 12 that is capable of acting on a medicament container 14 placed in the medicament delivery device 10. The medicament container 14 may be a syringe having an injection needle 16 in its proximal end. In order to protect the injection needle 16 and to keep it sterile before use, a medicament delivery member shield 18 may be placed surrounding the needle. The medicament delivery member shield 18 may be a so called rigid needle shield or RNS having an inner sheath 20 of resilient material such as rubber, and an outer shell 22 of harder or more rigid material such as polypropylene for instance. The RNS is further provided with an information carrier 24 that comprises data stored therein. Data could be information regarding the medicament, type, batch, manufacturing date, expiry date, etc. the information carrier comprises an antenna that enables reading of stored data from the tag by an information carrier reader. The antenna of the information carrier will in the following be named first antenna.

In this regard, the information carrier and the information carrier reader may comprise different technologies such as RFID-technology, NFC-technology and any other near range communication technologies that can transmit information wirelessly between at least two components provided with antennas.

The medicament delivery device is further arranged with a recording unit 26 that is releasably attached to a distal end of the medicament delivery device. The recording unit may be arranged with a number of elements and functions such as an electronic circuit with a processor capable of processing data program code for performing different tasks. Data program code may be stored in appropriate memory elements. The electronic circuit may further be arranged with some power supply such as button cells, photovoltaic panels, etc. Switching elements and sensors may further be arranged. The electronics circuit may further be arranged with a user communication circuit that may be arranged and programmed to communicate with a user. The user communication circuit may comprise display elements that can communicate visually, e.g. by text stored in the electronics module that is displayed on a suitable display on the recording unit. In addition to, or instead, the user communication circuit may comprise audio elements that can communicate audibly, e.g. by a recorded message stored in the electronics module that is played in an appropriate loudspeaker of the electronics module or of the device as such.

The recording unit 26 may further be arranged with at least one communication circuit. The communication circuit may be an information carrier reader such as an RFID-reader 28, provided with an RFID chip 30 and antenna 32. The antenna of the RFID-reader will in the following be named second antenna. The RFID-reader 28 may be used for monitoring the usage of the medicament delivery device such that information is transmitted from the medicament delivery device 10 to the recording unit 26. Further, monitored data obtained by the recording unit may be transferred to external storage sources and/or external devices.

Figure 3:
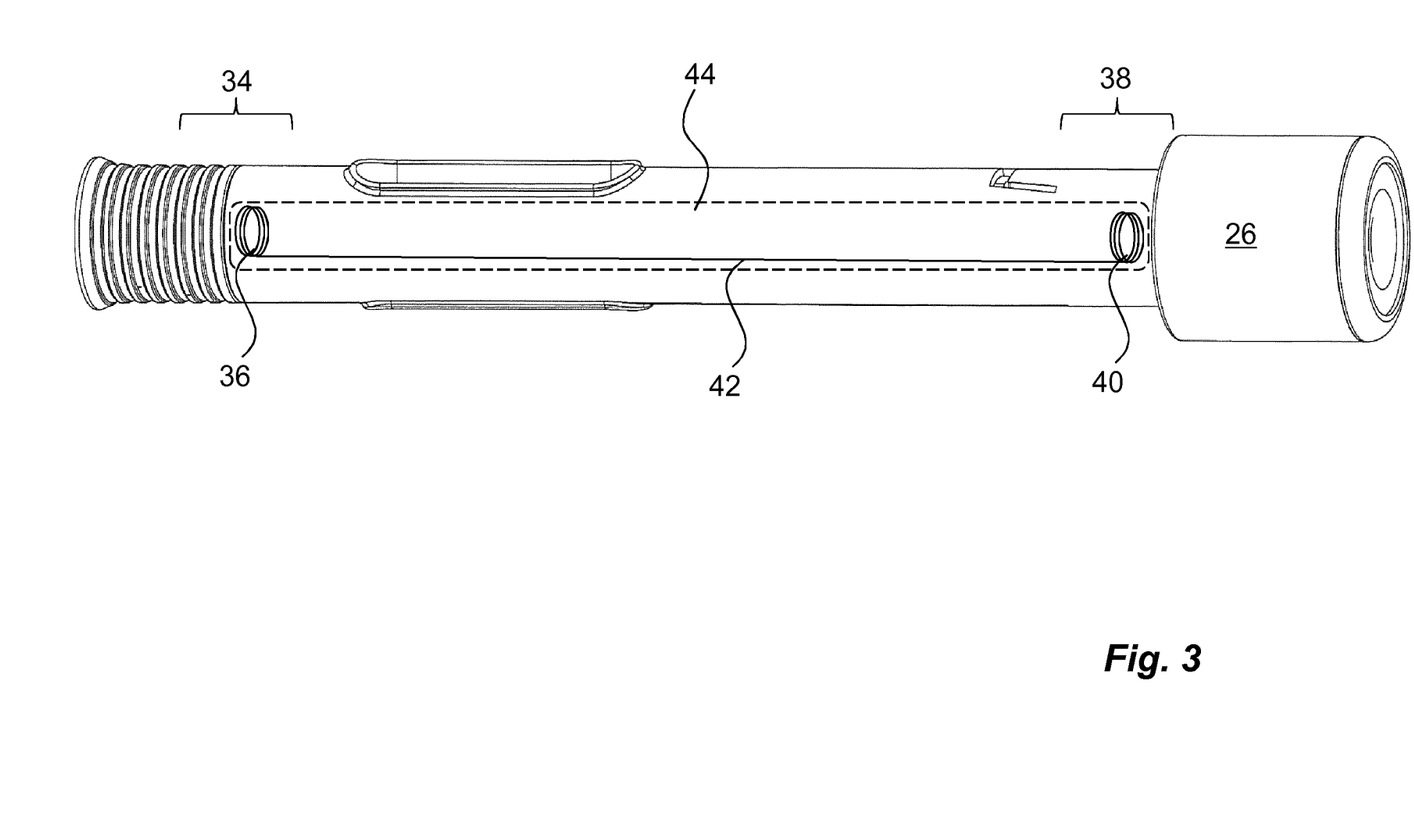
FIG. 3 shows one embodiment of an RFID-reader assembly arrangement.

According to one feasible solution for obtaining data from the information carrier such as an RFID-tag 24, a first proximal area or part 34, FIG. 3, of the medicament delivery device 10 is arranged with a third antenna 36 and a second distal area or part 38 of the medicament delivery device 10 is arranged with a fourth antenna 40. The third antenna 36 is connected to the fourth antenna 40 via suitable electrical conduits or connections 42, such as electrically conductive wiring. Thus the third antenna 36 is positioned in the vicinity of the first antenna of the information carrier 24 on the RNS 18 and the fourth antenna 40 is positioned in the vicinity of the second antenna 32 of the information carrier reader 28 of the recording unit 26. With this solution the recording unit 26 can now read the information carrier via the two interconnected third and fourth antennas.

According to a simple and cost-effective solution the third and fourth antennas can be coils of metal, such as copper, that work with inductive coupling to the information carrier and to the information carrier reader. With such a solution, a disposable medicament delivery device will not be much more expensive compared to a medicament delivery device without the extra antennas.

The third and fourth antennas and the wiring between these antennas may be made in a number of ways. One solution is to in-mould the antennas and the wiring into components of the medicament delivery device when the components are made. Another solution is to make at least the wiring with laser direct structuring on the surface of the medicament delivery device. A further cheap and efficient solution is to provide the antennas and the wiring on adhesive labels 44, FIG. 3, that are attached on the surface of the medicament delivery device. With this solution it is very easy and cost-efficient to arrange the antennas. The label may also be used in connection with detecting tampering attempts. For instance, the label may cross or cover a connection 45, FIG. 4, between two parts of a housing element containing the medicament container. If then someone tried to open the housing elements for accessing the medicament container for some reason, then the label would rupture in that area 47 and thus the wiring would be broken and a subsequent reading of the information carrier would not be possible, which in turn would indicate a tampering attempt.

Figure 4:
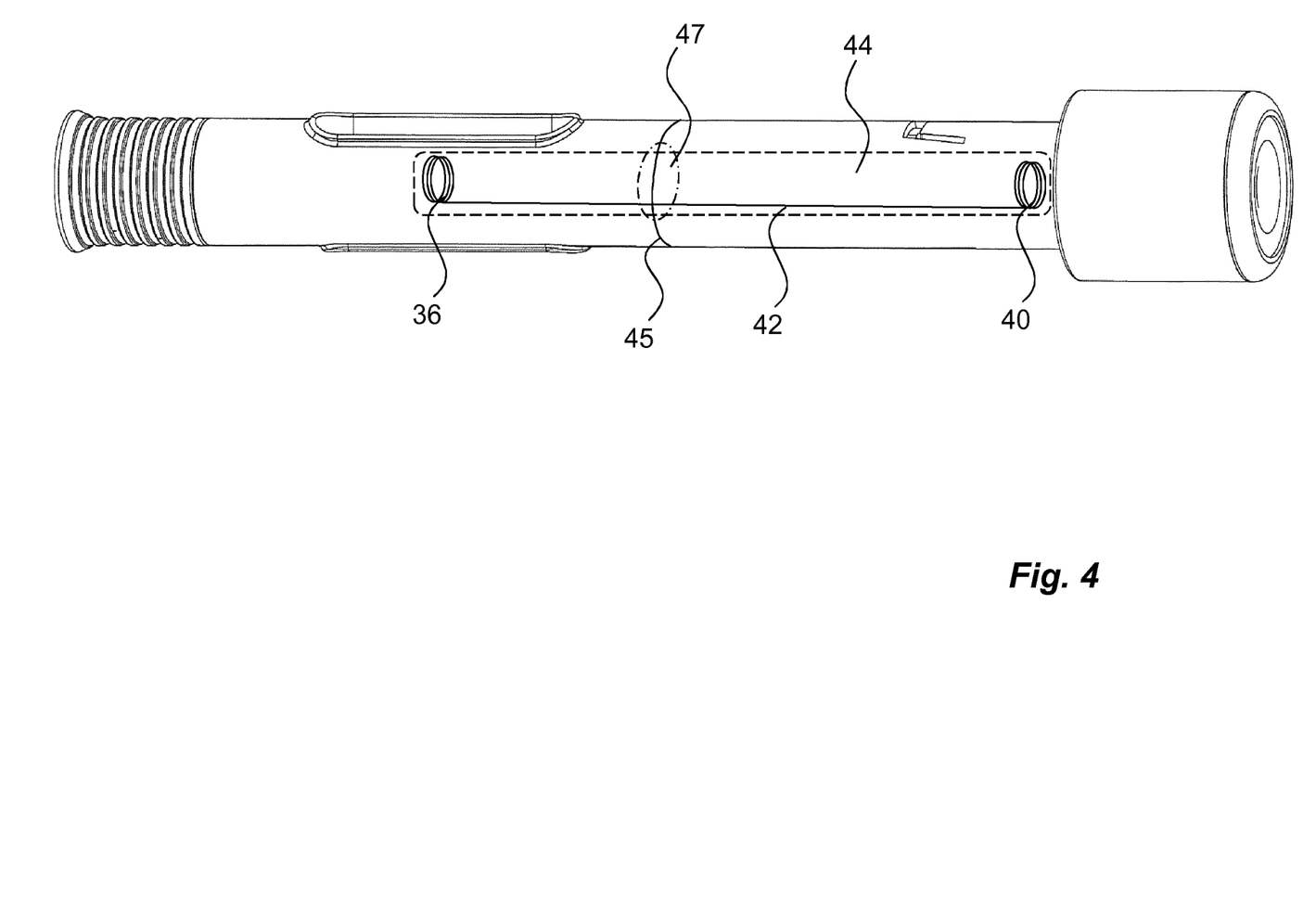
FIG. 4 shows a variant of the arrangement of FIG. 3.

The information carrier could be placed on other components than an RNS. For instance, a medicament container 14 may be provided with a label containing the information carrier 24. It is then an easy task to modify for instance a label 44 to have the first antenna 36 in the vicinity of the information carrier, as seen in FIG. 4.

Figure 5:
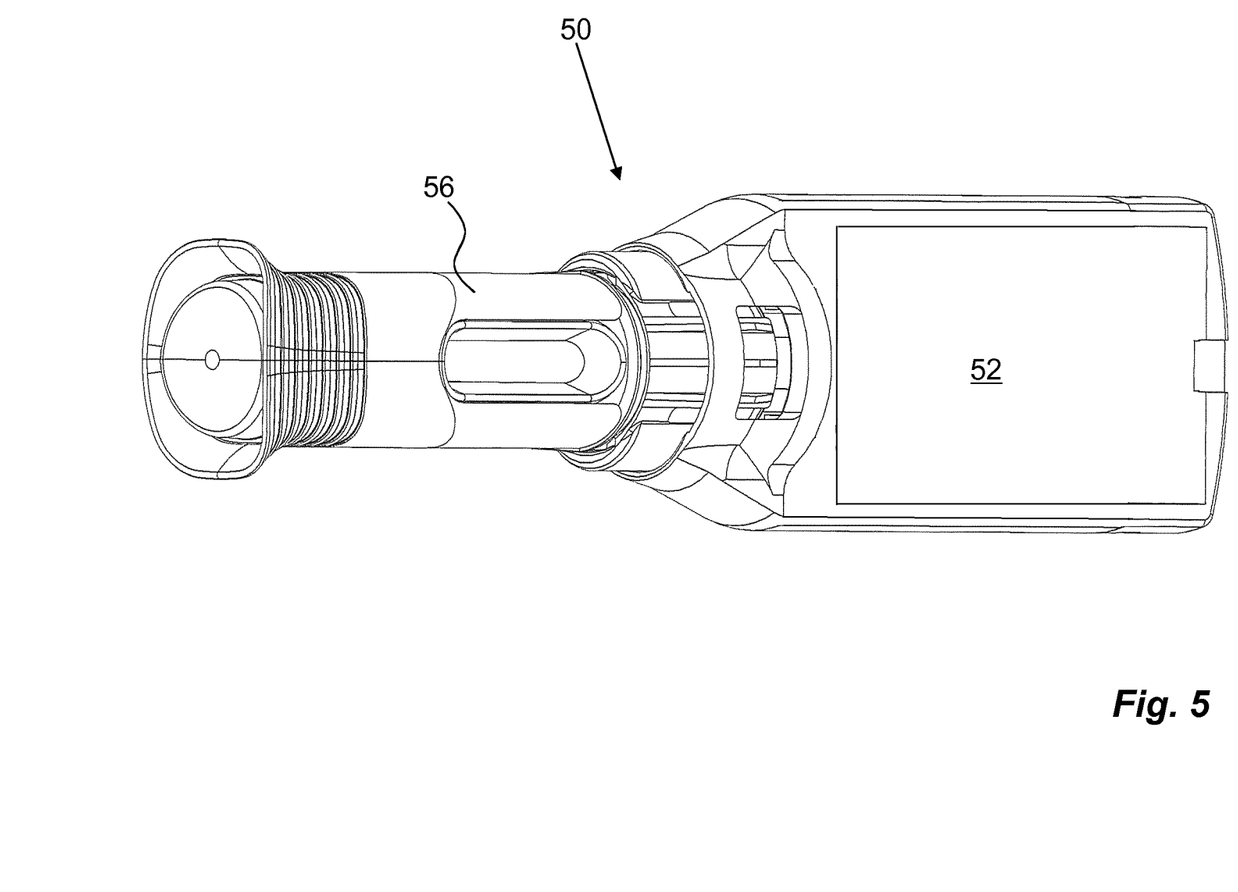
FIG. 5 shows another medicament delivery device which may comprise the present application.
Figure 6:
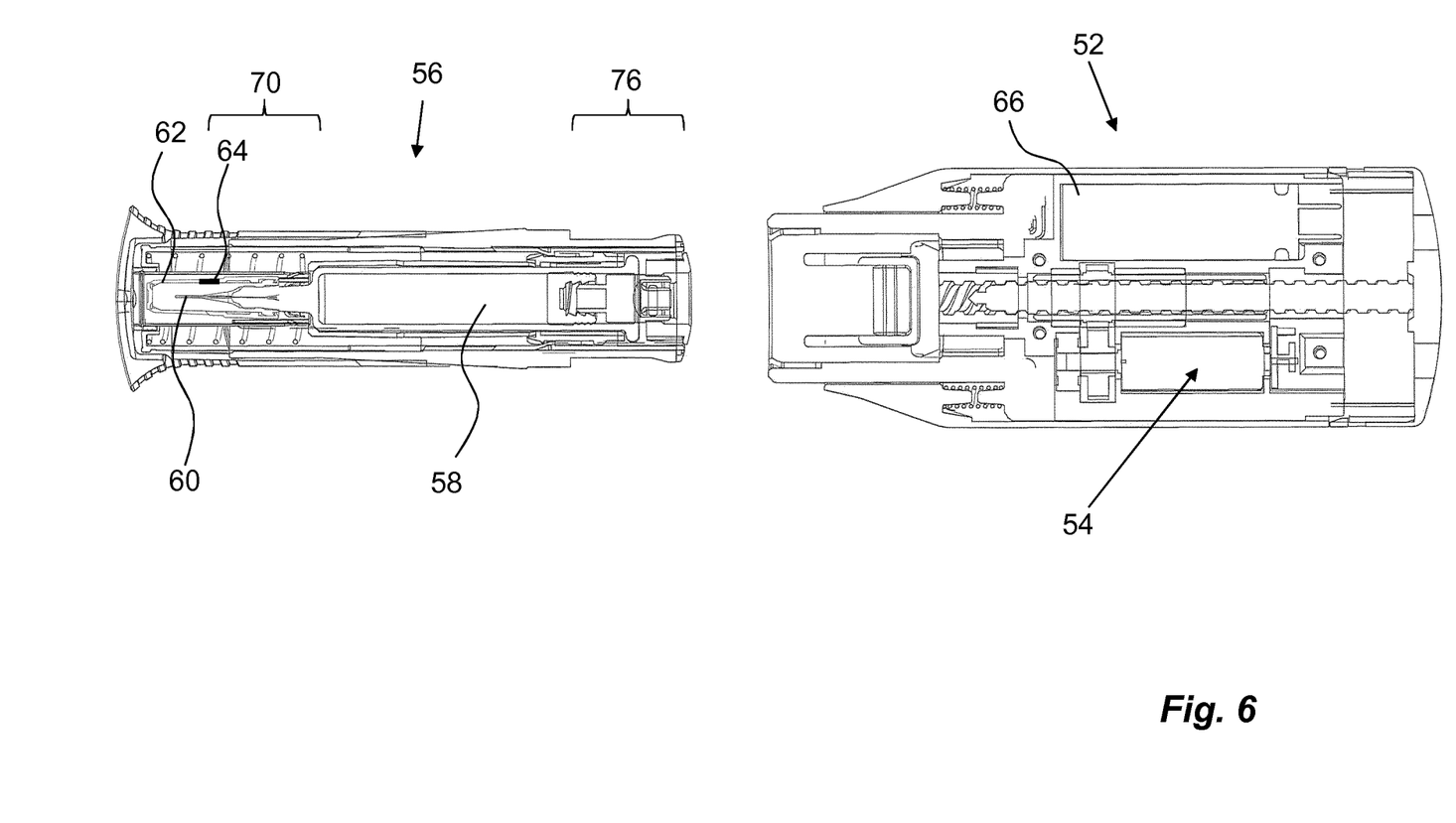
FIG. 6 shows a cross-section of the medicament delivery device according to FIG. 5.
Figure 7:
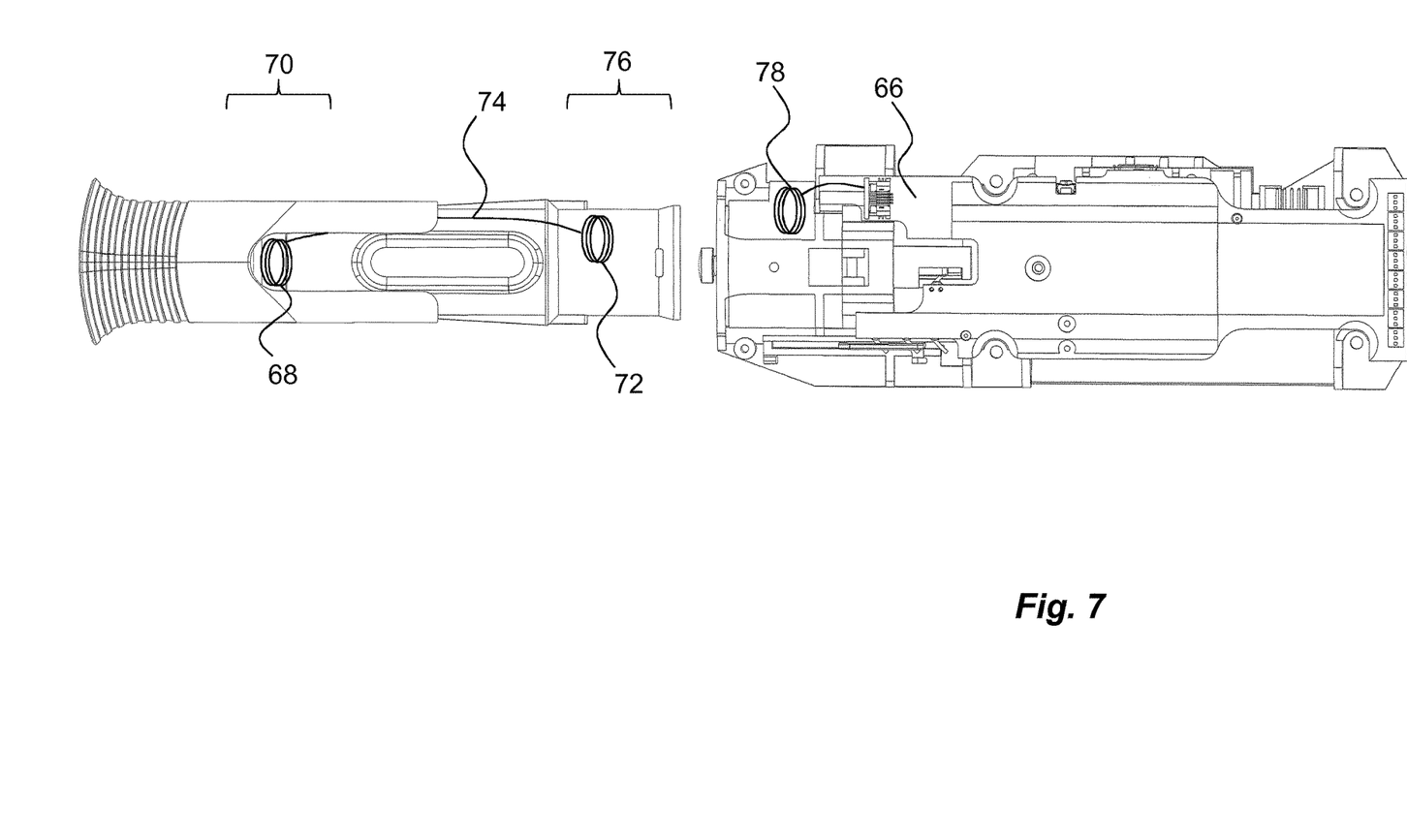
FIG. 7 shows another embodiment of an RFID-reader assembly arrangement.

Apart from disposable devices, there might be medicament delivery devices where it is difficult to place an information carrier reader close to an information carrier. FIGS. 5-7 show an example of a motor-driven medicament delivery device 50 having a main body 52 provided with a drive unit 54. The medicament delivery device 50 further comprises a cassette 56 or the like holder for accommodating a medicament container 58. In the embodiment shown, the medicament container 58 is a syringe with an injection needle 60, wherein the injection needle 60 is protected by an RNS 62. The cassette 56 is connectable to the main body 52, after which the drive unit 54 of the main body 52 may be activated to expel a dose of medicament.

In one solution the cassette is re-usable and the medicament container is replaced after a dose delivery sequence. In another solution the whole cassette is disposable and is discarded after a dose delivery sequence. In any event, if the RNS 62 of the medicament container 58 is arranged with an information carrier 64, there is a problem reading it with an information carrier reader 66 of the main body 52 due to the distance. Further, the connection between the cassette 56 and the main body 52 also poses problems with wiring to an antenna placed in the cassette 56 for enabling reading of the information carrier 64.

The solution according to the application is to provide a first antenna 68 in the cassette 56 in a first area or part 70 that is in the vicinity of the information carrier 64 and to provide a second antenna 72 in the cassette 56, interconnected with the first antenna 68 via wiring 74, in a second distal area or part 76 of the cassette 56, which second part 76 is designed with a connection structure for inter-connecting with the main body 52. Further, the main body 52 is designed such that an antenna 78 of the information carrier reader 66 is placed adjacent the connection structure of the main body 52. Thus, when activated, the first antenna 68 can read the information carrier 64, wherein the info is transferred to the second antenna 72 via the wiring 74, which data in turn is transferred from the second antenna 72 to the antenna 78 of the information carrier reader 66. With this solution, not only do the antennas extend the reading range but also provide a contactless transfer from the cassette 56 to the main body 52.

It is to be understood that the embodiments described above and the shown in the drawings are to be regarded only as non-limiting examples of the disclosure and that it may be modified in many ways within the scope of the patent claims.

The invention claimed is:

1. An information carrier reader assembly comprising:
a first antenna; and
a second antenna electrically connected to the first antenna,
wherein the first antenna is attached to a first area of a medicament delivery device that comprises an information carrier comprising a fourth antenna,
wherein the first antenna is positioned so as to enable transmission between the fourth and the first antenna,
wherein the information carrier reader assembly further comprises an information reader provided with a third antenna and being operably arranged to a second area of the medicament delivery device,
wherein the second antenna is attached to the second area of the medicament delivery device to enable a transmission between the second antenna and the third antenna,
wherein the first antenna is positioned adjacent a proximal end of the medicament delivery device,
wherein the second antenna positioned adjacent a distal end of the medicament delivery device,
wherein the first antenna, second antenna, third antenna, and fourth antenna are spaced a longitudinal distance along a length of the medicament delivery device apart from one another between the proximal end and the distal end of the medicament delivery device,
wherein the first antenna, second antenna, third antenna, and fourth antenna are enclosed inside the medicament delivery device, and
wherein the information carrier reader assembly is arranged in a separate unit releasably attachable to the medicament delivery device, wherein the third antenna of the information reader is configured to read the second antenna when the separate unit is connected to the medicament delivery device.

2. The information carrier reader assembly according to claim 1, wherein the first antenna is a metal coil configured to provide an inductive coupling with the fourth antenna of the information carrier and that the second antenna is a metal coil configured to provide an inductive coupling with the third antenna of the information reader.

3. The information carrier reader assembly according to claim 2, wherein the first antenna and the second antenna are interconnected by conductive conduits.

4. The information carrier reader assembly according to claim 3, wherein the first antenna, the second antenna and the conductive conduits are arranged on at least one adhesive label attachable to the medicament delivery device.

5. The information carrier reader assembly according to claim 4, wherein the at least one adhesive label comprises a rupturable area forming a tamper indicating element.

6. The information carrier reader assembly according to claim 3, wherein conductive conduits are formed on the medicament delivery device by laser direct structuring.

7. The information carrier reader assembly according to claim 1, wherein the information carrier reader assembly is arranged on a re-usable part of the medicament delivery device and that the first antenna and the second antenna are arranged on a disposable part of the medicament delivery device, and wherein the third antenna of the information carrier reader assembly is configured to read the second antenna when the disposable part is connected to the re-usable part.

8. The information carrier reader assembly according to claim 7, wherein the first antenna and the second antenna are spaced apart from one another along the length of the information carrier reader assembly when the disposable part is connected to the re-usable part.

9. A medicament delivery device comprising:
a first antenna attached to a first part of the medicament delivery device adjacent a proximal end of the medicament delivery device;
a second antenna electrically connected to the first antenna and attached to a second part of the medicament delivery device adjacent a distal end of the medicament delivery device, wherein the first part is arranged to accommodate a medicament container that comprises an information carrier readable by the first antenna; and
an information carrier reader assembly operably arranged to the second part, configured to communicate with the second antenna,
wherein the first antenna and the second antenna are spaced a longitudinal distance along a length of the medicament delivery device apart from one another between the proximal end and the distal end of the medicament delivery device,
wherein the first antenna and second antenna are enclosed inside the medicament delivery device,
wherein the information carrier reader assembly is arranged in a separate unit releasably attachable to the medicament delivery device, wherein a third antenna of the information reader is configured to read the second antenna when the separate unit is connected to the medicament delivery device.

* * * * *